United States Patent [19]

Van Broeck et al.

[11] Patent Number: 5,036,077
[45] Date of Patent: Jul. 30, 1991

[54] 1-(BENZYLPIPERIDINO)PROPAN-2-OL DERIVATIVES, THEIR PREPARATION, THEIR USE AS ANTIMICROBIAL AGENTS AND THE PRODUCTS IN WHICH THEY ARE PRESENT

[75] Inventors: Didier Van Broeck, Murviel les Montpellier par Pignan; Madeleine Mosse, Montpellier, both of France

[73] Assignee: Sanofi, Paris, France

[21] Appl. No.: 244,270

[22] Filed: Sep. 15, 1988

[30] Foreign Application Priority Data

Sep. 17, 1987 [FR] France .................. 87 12885

[51] Int. Cl.⁵ .................. A61K 31/445; C07D 401/00
[52] U.S. Cl. ...................... 514/317; 546/240
[58] Field of Search ................. 546/240; 514/317

[56] References Cited

U.S. PATENT DOCUMENTS 3,702,850 11/1972 Pedrazzoll et al. ............ 546/240
3,912,733 10/1975 Santilli ........................ 546/240
3,968,218 7/1976 Couillon ...................... 546/240
4,482,560 11/1984 Banno et al. .................. 546/240

OTHER PUBLICATIONS

Chemical Abstracts, vol. 100, 1984, 167725k, "Studies on the Local Anesthetics, etc.".
Proc. National Acad. Sci, U.S.A., vol. 72, No. 4, pp. 1564–1568, Apr. 1975, Alexander et al.

*Primary Examiner*—Mary C. Lee
*Assistant Examiner*—Robert C. Whittenbaugh
*Attorney, Agent, or Firm*—Foley & Lardner

[57] ABSTRACT

The invention relates to compounds of the formula:

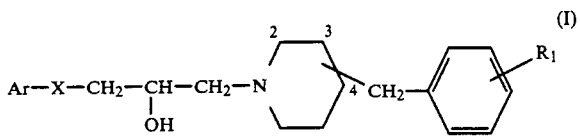

in which:
Ar represents a phenyl group substituted by $R_2$, $R_3$ and $R_4$, or a naphth-1-yl or naphth-2-yl group, unsubstituted or substituted by 1 or 2 halogen atoms;
X represents an oxygen atom or a sulfur atom;
$R_1$ represents H or a halogen atom;
$R_2$ represents a halogen atom, a trifluoromethyl group, a phenyl group which is unsubstituted by 1 or 3 halogen atoms, a benzyl group which is unsubstituted or substituted by 1 to 3 halogen atoms, a phenoxy group which is unsubstituted or substituted by 1 to 3 halogen atoms, or a $C_1$–$C_4$ alkyl group;
$R_3$ and $R_4$ represents H, a halogen atom or a $C_1$–$C_4$ alkyl group; and
the benzyl group substitutes the piperidino radical in the 2-, 3- or 4-position, and their salts with mineral or organic acids.

It also relates to a process for the preparation of said compounds and their use as antimicrobial agents, as antiseptic, disinfectant, preservative in different kinds of products (pharmaceutical compositions, cosmetics, agri-foodstuffs). It also relates to said products containing the compounds of formula (I).

11 Claims, No Drawings

1-(BENZYLPIPERIDINO)PROPAN-2-OL DERIVATIVES, THEIR PREPARATION, THEIR USE AS ANTIMICROBIAL AGENTS AND THE PRODUCTS IN WHICH THEY ARE PRESENT

The present invention relates to novel 1-(benzylpiperidino)propan-2-ol derivatives.

The present invention further relates to the use of the compounds according to the invention in antiseptic, antimicrobial and antifungal compositions as disinfectants or preservatives, especially in the sectors of pharmacy, cosmetology or agri-foodstuffs.

In another aspect, the present invention relates to the process for the preparation of the compounds according to the invention.

Numerous 1-amino-3-aryloxypropan-2-ol derivatives are known and have been described for their cardiovascular activities, especially their beta-adrenergic properties. An example which may be mentioned to illustrate this chemical series is propranolol, which has the following formula:

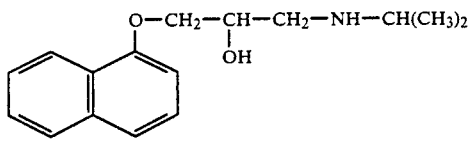

Furthermore, 1-piperidino-3-aryloxypropan-2-ol derivatives have been described.

The French patent published under no. 1 548 392 describes compounds of the formula:

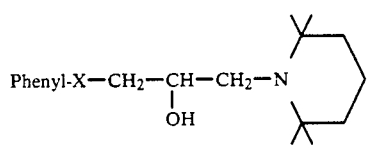

in which X=O or S and the phenyl radical optionally carries a substituent.

The German patent published under no. 2 348 898 describes compounds of the formula:

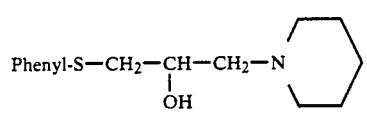

The Japanese article by IGARASHI HARUYOSHI et al., Shika Kiso Igakkai Zasshi, 1983, 25 (4), 867-74 (Chemical Abstracts 100, 167725) describes compounds of the formula:

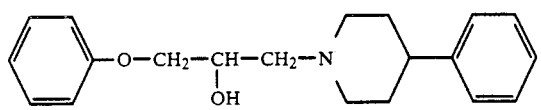

According to the present invention, novel 1-(benzylpiperidino)propan-2-ol derivatives have been found which have antimicrobial properties.

Thus the present invention relates to novel 1-(benzylpiperidino)propan-2-ol derivatives of the formula:

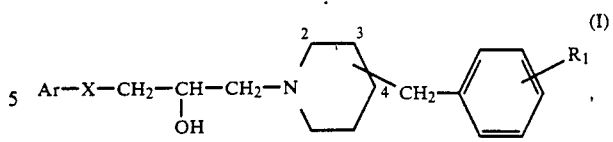

in which:
Ar represents a phenyl group substituted by $R_2$, $R_3$ and $R_4$, or a naphth-1-yl or naphth-2-yl group, the said naphthyl groups being unsubstituted or substituted by 1 or 2 halogen atoms;
X represents an oxygen atom or a sulfur atom;
$R_1$ represents a hydrogen atom or a halogen atom;
$R_2$ represents a halogen atom, a trifluoromethyl group, a phenyl group which is unsubstituted or substituted by 1 to 3 halogen atoms, a benzyl group which is unsubstituted or substituted by 1 to 3 halogen atoms, a phenoxy group which is unsubstituted or substituted by 1 to 3 halogen atoms, or an alkyl group containing from 1 to 4 carbon atoms;
$R_3$ and $R_4$ represent hydrogen, a halogen atom or an alkyl group containing from 1 to 4 carbon atoms; and
the benzyl group substitutes the piperidino radical in the 2-, 3- or 4-position,
and to their salts with mineral or organic acids such as hydrochloric acid, phosphoric acid, sulfuric acid, alkylsulfonic acids like methanesulfonic acid or laurylsulfonic acid, and isethionic acid.

The compounds (I) contain an asymmetric carbon; the present invention includes each of the enantiomers of the compounds (I) as well as the racemates.

The present invention further relates to the process for the preparation of the compounds of formula (I), which comprises treating the epoxide of the formula:

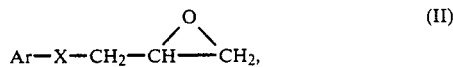

in which Ar and X have the meanings indicated above, with the benzylpiperidine of the formula:

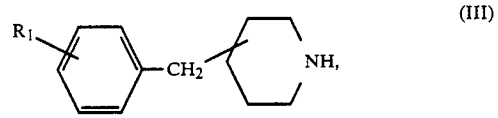

in which $R_1$ has the meaning indicated above and the benzyl group substitues the piperidine in the 2-, 3- or 4-position, in a protic solvent, at a temperature between room temperature and the boiling point of the solvent, and isolating the compound (I) in the form of a free base or in the form of a salt with a mineral or organic acid.

The reaction is advantageously carried out with an equimolecular amount of the 2 reactants or in the presence of an excess of the epoxide (II).

Examples of protic solvents which can be used are water or a primary alcohol such as methanol, ethanol, isopropanol or methoxyethanol.

The reaction for the formation of (I) is complete after a time of between 1 hour and 48 hours, depending on the operating conditions.

The epoxides (II) are known or prepared by known methods. Thus (II) can be prepared by treating a compound of the formula:

Ar-X-H     (IV)

in which Ar and X have the meanings indicated above, with 1-chloro-2,3-epoxypropane or 1-bromo-2,3-epoxypropane, in a solvent in a basic medium.

It is possible, for example, to prepare an epoxide (II) by reacting an excess of 1-chloro-2,3-epoxypropane with a solution of a compound (IV) in a ketone solvent such as butanone, in the presence of potassium carbonate.

The benzylpiperidines (III) are known or prepared by known methods. Thus a benzylpiperidine (III) can be prepared from the corresponding benzylpyridine by catalytic hydrogenation.

The following Examples illustrate the invention without however limiting it.

EXAMPLE 1

1-(4-Benzylpiperidino)-3-(2,4-dichlorophenoxy)propan-2-ol

SR 44333

(A) 3-(2,4-Dichlorophenoxy)-1,2-epoxypropane

A mixture containing 81.5 g of 2,4-dichlorophenol in 120 g of 1-chloro-2,3-epoxypropane and 138 g of potassium carbonate is refluxed for 10 hours.

The inorganic salts formed are filtered off and drained. The clear filtrate is evaporated under vacuum and the oily residue is distilled under 0.01 mm of mercury to give the expected product in the form of a colorless oil.

Boiling point: 124°–126° C.
Weight: 82 g
Yield: 75%

(B) SR 44333

A solution containing 8.75 g of 4-benzylpiperidine and 11.5 g of the epoxide prepared in the previous step, in 100 ml of methanol, is stirred for 48 hours at room temperature.

The colorless clear solution formed is evaporated to half its volume to cause crystallization, this is completed by cooling in ice and the white crystals formed are then filtered off, washed quickly with iced methanol and dried under vacuum.

This gives 12.65 g of the expected product.
Yield: 64%
Melting point: 88°–90° C.

| Elemental analysis: | C | H | N | Cl |
|---|---|---|---|---|
| calculated | 63.96 | 6.39 | 3.55 | 17.98 |
| found | 64.10 | 6.54 | 3.59 | 17.76 |

(C)
1-(4-Benzylpiperidino)-3-(2,4-dichlorophenoxy)propan-2-ol methanesulfonate

SR 44333 B 10 g of SR 44333 are dissolved in 200 ml of ether, with warming of the solution, and 2.44 g of methanesulfonic acid in 50 ml of ether are added slowly; the salt solidifies. The mixture is stirred for 2 hours and the white crystals are then filtered off, washed with ether and dried under vacuum.

Weight: 12.25 g
Yield: 98.6%
Melting point: 116°–118° C.

| Elemental analysis: | C | H | N | Cl |
|---|---|---|---|---|
| calculated | 53.88 | 5.96 | 2.85 | 14.46 |
| found | 54.03 | 6.10 | 2.70 | 14.46 |

(D)
1-(4-Benzylpiperidino)-3-(2,4-dichlorophenoxy)propan-2-ol hydrochloride

SR 44333 A 12.8 g of the free base are dissolved in 150 ml of acetone. A sufficient amount of a solution of hydrogen chloride in ether is added dropwise. The salt crystallizes rapidly in the form of white crystals.

Weight obtained: 12.05 g
Yield: 93.3%
Melting point: 144°–146° C.

| Elemental analysis: | C | H | N | Cl |
|---|---|---|---|---|
| calculated | 58.55 | 6.08 | 3.25 | 24.69 |
| found | 58.68 | 6.21 | 3.16 | 24.54 |

EXAMPLE 2

3-(2-Benzyl-4-chlorophenoxy)-1-(4-benzylpiperidino)-propan-2-ol hydrochloride

SR 44719 A (A) 3-(2-Benzyl-4-chlorophenoxy)-1,2-epoxypropane

A suspension containing 21.87 g of 2-benzyl-4-chlorophenol, 27.76 g of 1-chloro-2,3-epoxypropane and 27.64 g of potassium carbonate in 200 ml of butanone is refluxed for 12 hours. The inorganic salts formed are filtered off and drained. The solvent and excess 1-chloro-2,3-epoxypropane are evaporated off under vacuum and the residue is distilled at between 160° C. and 180° C. under 0.01 mm of mercury.

The colorless oil obtained solidifies rapidly.
Weight: 21.7 g
Yield: 79%

(B) SR 44719 A

A solution containing 11.6 g of the epoxide obtained in the previous step and 7 g of 4-benzylpiperidine in 100 ml of methanol is stirred at room temperature for 48 hours. The methanol is driven off under vacuum and the residue is then taken up with 200 ml of acetone and treated with a sufficient amount of a solution of hydrogen chloride in ether. The white crystals formed are filtered off, washed with an acetone/ether mixture and dried under vacuum.

Weight: 16.3 g
Yield: 83.8%
Melting point: 139°–141° C.

| Elemental analysis: | C | H | N |
|---|---|---|---|
| calculated | 69.13 | 6.84 | 2.88 |
| found | 68.98 | 7.06 | 2.78 |

EXAMPLE 3

1-(4-Benzylpiperidino)-3-(4-bromophenylthio)propan-2-ol hydrochloride

SR 44444 A (A) 3-(4-Bromophenylthio)-2,3-epoxypropane

A suspension containing 9.45 g of 4-bromothiophenol, 14.45 g of 1-chloro-2,3-epoxypropane and 13.8 g of potassium carbonate in 100 ml of butanone is refluxed for 12 hours. The inorganic salts formed are filtered off and drained and the solvent and excess 1-chloro-2,3-epoxypropane are then evaporated off under vacuum. The residual oil is distilled at between 130° C. and 140° C. under 0.01 mm of mercury.

Weight obtained: 10.43 g
Yield: 85%

(B) SR 44444 A

This product is prepared by following the same procedure as in the previous Examples, starting from 2.6 g of the epoxide obtained in step A and 1.75 g of 4-benzylpiperidine.

The hydrochloride formed is crystallized from acetone.

Weight obtained: 4.41 g
Yield: 97%
Melting point: 158°–160° C.

| Elemental analysis: | C | H | N |
| --- | --- | --- | --- |
| calculated | 55.21 | 5.96 | 3.06 |
| found | 55.29 | 6.04 | 2.94 |

EXAMPLE 4

1-(4-Benzylpiperidino)-3-(1-bromonaphth-2-yloxy)propan-2-ol hydrochloride

SR 44716 A (A) 3-(1-Bromonaphth-2-yloxy)-1,2-epoxypropane

A suspension containing 22.3 g of 1-bromonaphth-2-ol, 27.75 g of 1-chloro-2,3-epoxypropane and 27.6 g of potassium carbonate in 200 ml of butanone is refluxed overnight. The inorganic salts are filtered off and drained and the filtrate is then evaporated under vacuum. The oil obtained is distilled under 0.01 mm of mercury.

Weight obtained: 22.63 g
Yield: 81%
Boiling point: 165°–185° C.

(B) SR 44716 A

By following the same procedure as in the previous Examples, starting from 2.93 g of the epoxide obtained in step A and 1.75 g of 4-benzylpiperidine in 25 ml of methanol, the expected product is obtained; after salification it crystallizes from acetone in the form of white crystals.

Weight: 3.99 g
Yield: 81.3%
Melting point: 159°–161° C.

| Elemental analysis: | C | H | N |
| --- | --- | --- | --- |
| calculated | 61.17 | 5.75 | 2.85 |
| found | 61.36 | 6.00 | 2.74 |

EXAMPLE 5

1-(3-Benzylpiperidino)-3-(2,4-dichlorophenoxy)propan-2-ol methanesulfonate

SR 44957 A (A) 3-(2,4-Dichlorophenoxy)-1,2-epoxypropane

This product is prepared in Example 1, step A.

(B) 4-(Parachlorobenzyl)piperidine

This product is prepared by following the method described in US patent 3 682 767.

0.2 ml of 4-(parachlorobenzyl)pyridine is dissolved in 500 ml of citric acid, 3.7 g of platinum oxide are added and the mixture is placed in an autoclave under a hydrogen pressure of 4 bar and stirred for 7 hours. 0.5 g of platinum oxide is added and the mixture is placed under a hydrogen atmosphere for 5 hours.

After the catalyst has been filtered off, the filtrate is concentrated to dryness under vacuum and the residue is taken up in iced water and then rendered basic (pH=10–11) by the addition of a 10% solution of sodium hydroxide and then a 30% solution of sodium hydroxide.

Extraction with ethyl acetate and drying over magnesium sulfate gives an oil, which crystallizes on the addition of a solution of hydrogen chloride in ether.

Weight obtained: 43.4 g
Yield: 88%

(C) SR 44957 A

This product is prepared according to the method described in the previous Examples.

The methanesulfonate crystallizes from ether.
Melting point: 114°–116° C.

The compounds according to the invention which are described in Table I below were prepared by following the same procedure.

TABLE I

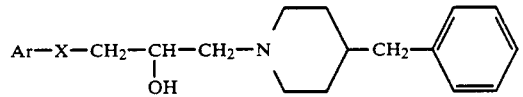

$$Ar-X-CH_2-CH(OH)-CH_2-N\diagup\!\!\!\!\diagdown\!\!-CH_2-\text{phenyl}$$

| Product number (Example no.) | Ar | X | Salt Melting point | (formation solvent) |
| --- | --- | --- | --- | --- |
| SR 44251 A (6) | 4-bromophenyl | O | hydrochloride 176–178° C. | (ether) |
| SR 44334 A (7) | 4-chlorophenyl | O | hydrochloride 146–148° C. | (acetone) |
| SR 44473 A (8) | 3,4-dichlorophenyl | S | hydrochloride 150–152°C. | (acetone) |
| SR 44560 A (9) | 2,4,5-trichlorophenyl | O | hydrochloride 144–146° C. | (acetone/ether) |
| SR 44641 A (10) | 5-chloro-2-(2,4-dichlorophenoxy)-phenyl | O | hydrochloride 134–136°C. | (ether) |
| SR 44644 A (11) | naphth-1-yl | O | hydrochloride 199–201° C. | (acetone) |
| SR 44644 B (12) | naphth-1-yl | O | methane sulfonate 141–143° C. | (acetone) |

TABLE I-continued

Ar—X—CH$_2$—CH(OH)—CH$_2$—N(piperidine)—CH$_2$—(phenyl)

| Product number (Example no.) | Ar | X | Salt Melting point | (formation solvent) |
|---|---|---|---|---|
| SR 44648 A (13) | 4-tert-butylphenyl | O | hydrochloride 181–183° C. | (acetone) |
| SR 44674 A (14) | 4-bromo-naphth-2-yl | O | hydrochloride 190–192° C. | (acetone) |
| SR 44676 A (15) | 2-phenyl-phenyl | O | hydrochloride 139–141° C. | (acetone) |
| SR 44715 A (16) | 4-phenyl-phenyl | O | hydrochloride 177–179° C. | (acetone) |
| SR 44715 B (17) | 4-phenyl-phenyl | O | methane-sulfonate 152–154° C. | (acetone) |
| SR 44719 B (18) | 2-benzyl-4-chlorophenyl | O | methane-sulfonate 124–126° C. | (ether) |
| SR 44807 A (19) | naphth-2-yl | O | methane-sulfonate 135–137° C. | (acetone/ether) |
| SR 44971 A (20) | 2,4-difluoro-phenyl | O | hydrochloride 123–125° C. | (acetone/ether) |
| SR 44999 A (21)** | naphth-1-yl | O | methane-sulfonate 181–183° C. | (acetone/ether) |
| SR 45076 A (22)** | 4-bromophenyl | S | hydrochloride 167–169° C. | (acetone) |
| SR 45077 A (23)** | 3,4-dichloro-phenyl | S | hydrochloride 134–136°C. | (acetone) |
| SR 45204 A (24) | 3-bromophenyl | S | hydrochloride 129–131° C. | (acetone) |
| SR 45236 A  SR 45237 A (25 & 26)* | 3,4-dichloro-phenyl | S | hydrochloride 129–131° C. 113–115° C. | (acetone) (acetone/ether) |
| SR 45551 A (27) | 3,4-dichloro-phenyl | O | hydrochloride 151–153° C. | (acetone/ether) |
| SR 45553 A (28)** | 3,4-dichloro-phenyl | O | hydrochloride 139–140° C. | (acetone/ether) |

*The benzyl group substitutes the piperidino radical in the 3-position. SR 45236 A and SR 45237 A are the 2 diastereoisomers separated by chromatography on a silica column.
**The compounds of Examples 21, 22, 23 and 28 carry a parachloro substituent R$_1$ on the benzyl.

The bactericidal and fungicidal activities of the products according to the invention were studied on different strains.

A bacterial inoculum is brought into contact with different dilutions of the test product for a limited time of 30 minutes. When the contact time has ended, an aliquot of the bacterial suspension/product mixture is deposited on the surface of a gelose culture medium containing an agent for neutralizing the antibacterial activity of the product. The bactericidal concentration chosen is the minimum concentration of the product which is necessary to prevent bacterial growth. This concentration is expressed in μg/ml.

The bacterial strains chosen for the study are:
1 - Staphylococcus aureus CNCM 53154;
2 - Streptococcus faecalis CNCM 5855;
3 - Pseudomonas aeruginosa CNCM A22;
4 - Escherichia coli CNCM 54127.

The strains are maintained on Tryptic Soy Agar (TSA) marketed by Difco.

After 24 hours of culture at 37° C., the microbial growth is harvested with the aid of glass beads and 10 ml of diluent containing 1 g of tryptone and 8.5 g of sodium chloride in 1000 ml of distilled water. The suspension formed is shaken and the percentage transmission of light at 620 nm is measured on a spectrophotometer:
Strain 1: 60%;
Strain 2: 60%;
Strain 3: 70%;
Strain 4: 70%.

The bacterial inoculum corresponds to a 1/20 dilution of this bacterial suspension.

Plates containing cups receive different dilutions of the test product. These dilutions of the test product are brought into contact with the different bacterial suspensions using a multiple-site inoculator. After a contact time of 30 minutes, aliquots are transferred by means of this inoculator to the surface of a gelose medium (TSA) placed in petri dishes and containing an agent for neutralizing the activity, namely 20 g of lubrol W, 2.5 g of Tween 80, 2.5 g of sodium thiosulfate and 1% of egg yolk in 1000 ml of TSA (Difco). A reference for the efficacy of the neutralizing agent is prepared for each test product by depositing an aliquot of the dilution of the test product on the surface of the culture medium. After drying, the corresponding inoculum is deposited in the same place. A reference inoculum is prepared on a gelose medium with and without neutralizing agent. The results are read off after 48 hours of incubation at 37° C.

The antifungal activity of the products according to the invention was also determined using the method described above. The representative strain of yeast selected for the study was Candida albicans CNCM 1180 (strain 5).

This is maintained on a gelose medium of Sabouraud Dextrose Agar, marketed by Difco. The technique is identical to that described for studying the antibacterial activity. After 48 hours of culture at 37° C., the microbial growth is harvested with the aid of glass beads and 5 ml of diluent containing 1 g of tryptone and 8.5 g of sodium chloride in 1000 ml of distilled water; a further 5 ml of the diluent are then added. In a spectrophotometer, this suspension gives a 2 to 3% transmission of light at 620 nm. The inoculum corresponds to a 1/10 dilution of this microbial suspension. A 1/100 dilution of this suspension, observed between a microscope slide and cover slip through a lens of magnification 40, should show 10 cells per field, which corresponds to 1 000 000 yeasts per ml.

The results are collated in Table II below. They indicate the minimum bactericidal concentrations (MBC) for strains 1, 2, 3 and 4 and the minimum fungicidal concentrations (MFC) for strain 5.

By way of comparison, 3-aryloxy-1-piperidinopropan-2-ol derivatives described in the literature, or similar to the compounds described, were prepared and the bactericidal and fungicidal activities of these compounds and of propranolol were measured on the same strains and under the same conditions as for the products according to the invention. The results are reported in Table II after those obtained with the products according to the invention.

The comparison products are as follows:
Product A: 3-(4-bromophenoxy)-1-(4-methylpiperidino)propan-2-ol hydrochloride
Melting point: 194°–196° C.
Product B: 3-phenoxy-1-(4-phenylpiperidino)propan-2-ol hydrochloride
Melting point: 151°–153° C.

Product C: 3-(4-bromophenylthio)-1-piperidinopropan-2-ol hydrochloride
Melting point: 152°-154° C.
Propranolol

TABLE II

| Product no. (solubilizing agent) | MBC/MFC in μg/ml Strain | | | | |
|---|---|---|---|---|---|
| | 1 | 2 | 3 | 4 | 5 |
| SR 44251 A (water) | 100 | 100 | 100 | 100 | — |
| SR 44333 A (TEG) | 100 | 100 | 50 | 50 | — |
| SR 44333 B (water) | 50 | 50 | 50 | 50 | 50 |
| SR 44334 A (TEG) | 500 | 100 | 100 | 100 | — |
| SR 44444 A (TEG) | 50 | 50 | 50 | 50 | — |
| SR 44473 A (TEG) | 1000 | 50 | 50 | 50 | 50 |
| SR 44560 A (TEG) | 10 | 50 | 50 | 5 | 50 |
| SR 44641 A (acetone) | 50 | 10 | 10 | 5 | 50 |
| SR 44644 A (TEG) | 50 | 50 | 50 | 50 | 50 |
| SR 44648 A (acetone) | 200 | 200 | 50 | 50 | 200 |
| SR 44674 A (acetone) | 10 | 10 | 10 | 10 | 200 |
| SR 44676 A (TEG) | 200 | 50 | 10 | 10 | 50 |
| SR 44715 A (TEG) | 50 | 50 | 50 | 50 | 200 |
| SR 44716 A (TEG) | 50 | 50 | 10 | 10 | 50 |
| SR 44719 A (acetone) | 10 | 10 | 10 | 5 | 50 |
| SR 44719 B (TEG) | 10 | 5 | 10 | 5 | 10 |
| SR 44807 A (water) | 1000 | 1000 | 200 | 200 | 1000 |
| SR 44957 A (TEG) | 50 | ≦10 | ≦10 | ≦10 | 50 |
| SR 44971 A (TEG) | 1000 | 1000 | 1000 | 1000 | 1000 |
| SR 44999 A (TEG) | 50 | ≦10 | ≦10 | ≦10 | ≦10 |
| SR 45076 A (TEG) | 50 | 10 | 50 | 10 | 50 |
| SR 45077 A (TEG) | 50 | 10 | 50 | 10 | 50 |
| SR 45204 A (TEG) | >200 | >200 | 50 | 50 | >200 |
| SR 45236 A (TEG) | >200 | 50 | 50 | 50 | >200 |
| SR 45237 A (TEG) | >200 | 50 | 50 | 50 | >200 |
| SR 45551 A (TEG) | >200 | 50 | 50 | 50 | >200 |
| SR 45552 A (TEG) | >200 | 50 | 50 | 10 | 50 |
| SR 45553 A (TEG) | 10 | 50 | 50 | 10 | 50 |
| Product A (water) | >2000 | 1000 | 1000 | 1000 | 5000 |
| Product B (water) | >1000 | >1000 | >1000 | >1000 | >1000 |
| Product C (water) | >1000 | >1000 | >1000 | >1000 | 1000 |
| Propranolol (water) | 5000 | 1000 | 1000 | 1000 | 5000 |

The abbreviation TEG denotes a 20% solution of tetraethylene glycol in water.

The results show that the products according to the invention exhibit a broad spectrum of activity on the bacterial strains and fungal strain tested. This activity is expressed in a short time (less than or equal to 30 minutes).

By contrast, products A, B and C and propranolol exhibit no antimicrobial activity.

Experiments were also carried out to determine whether the compounds according to the invention had any activity on the cardiovascular system.

In particular, the affinity of these compounds for $\beta$-adrenergic receptors was studied by a biochemical technique.

The method used is the one described by R. W. Alexander, L. T. Williams and R. J. Lefkowitz, Proc. Nat. Acad. Sci. USA, 1975, 72 (4), 1564–1568.

On a preparation of membrane homogenates of dog heart and rat lung which contain $\beta_1$- and $\beta_2$-adrenergic receptors, the affinity of the test products for the binding sites is measured by competition with a radioactive ligand: tritiated dihydroalprenolol.

The affinity of the compounds according to the invention for adrenergic receptors was found to be 1000 to 10 000 times lower than that of propranolol.

The compounds according to the invention appear to have no beta-adrenergic activity.

Thus the compounds according to the invention represent a family of novel compounds which differ from the known compounds both in their novel chemical structure and in their activity.

The tolerance of the products according to the invention was studied on guinea-pigs. The animals are shaved on either side of the median line of the back and shaved again every 2 days. Groups of 6 animals receive, on the shaved area, 0.2 ml of an aqueous or alcoholic solution of the product according to the invention. When the products are in alcoholic solution, a control group of animals receives alcohol on one side.

To study the skin tolerance, the treatment is applied once a day for 6 out of 7 days over 3 weeks. The observations concerning the skin relate to the presence of erythema, skin eruption or hyperkeratosis, the intensity of which is graded according to a given scale.

The skin sensitization test is carried out on the same animals after a break of two weeks. The treatment lasts one week and is identical to the above. The results are evaluated against the same criteria and according to the same scale as that used for local tolerance.

The products according to the invention were found to be well tolerated when applied at concentrations ranging up to 2%. Furthermore, they exhibit no sensitizing effect.

The acute oral toxicity was evaluated on mice. This study was performed on male mice of the CD1 strain and of the Charles River breed. Each group was made up of 5 animals with a body weight varying from 24 to 30 g, kept in the same cage. The animals were fasted for 6 hours before the treatment. For each study, a suspension of the product in a 10% solution of gum arabic was administered by gavage with the aid of an esophageal tube. The animals were given food again 4 hours after gavage and were kept under observation for a period of 14 days after administration. During this period, the mortality in each of the experimental groups is noted and, where possible, the 50% lethal dose $LD_{50}$) is determined using the method of J. T. LITCHFIELD and R. WILCOXON, J. Pharmacol. 1949, 95, 99–113. The $LD_{50}$ per os of the products according to the invention was found to be greater than 1000 mg/kg.

The products according to the invention which have a good antimicrobial activity can be used in pharmaceutical, disinfectant, cosmetic or food preparations, especially as local and general antiseptics, as disinfectants and as preservatives.

As antiseptics for human or veterinary use, the concentration of active product can vary from 0.01% to 5% according to the use and the chosen formulation. Thus it is possible to prepare detergent foaming solutions which the surgeon and nursing staff can use to wash their hands or which is intended for cleansing dermatological lesions such as impetigo, pityriasis and leg ulcers. Detergent foaming solutions are also used as shampoos (for example antidandruff shampoos) or for the preparation of shower gels, shaving creams and foaming lotions. Foaming solutions containing products according to the invention are obtained by using amphoteric, anionic, cationic or non-ionic surfactants at a concentration of 0.3 to 30%, 0 to 20% of humectants such as glycols or polyethylene glycols, 0 to 20% of polypropylene/ethylene oxide copolymers, 0 to 15% of an alcohol (ethanol, isopropanol, benzyl alcohol) or a polyol such as glycerol, and also agents for complexing $Ca++$ and $Mg++$ ions, heavy metals, salts for providing an appropriate buffer capacity, agents for imparting viscosity, such as NaCl or KCl, natural, cellulosic or synthetic polymers, such as polyvinylpyrrolidone, superfatting agents with a thickening action, such as polyethylene glycol distearate and copra monoethanolamide or diethanolamide, fragrances, preservatives and colorants.

If the product according to the invention is not readily soluble in water, it is possible to use microemulsions, micellar solutions or any other phase of the ternary or quaternary diagram of water/active principle/surfactant/co-surfactant which permits solubilization in water. These solutions may or may not be diluted; they can be dispensed for example with the aid of a vasopump or liquefied or non-liquefied propellant gases.

With the same constituents at appropriate concentrations, products according to the invention can also be used to prepare simple aqueous solutions or aqueous solutions in the form of sprays intended for rendering operative fields antiseptic, for postoperative treatments or for treating burns, superinfected eczema, gluteal erythema, wounds or acne, or intended for deodorants.

Simple alcoholic solutions or alcoholic solutions in the form of sprays containing 20 to 80% of alcohol can contain, apart from the excipients used in aqueous solutions, excipients which make it possible to penetrate the keratinized layers of the skin and superficial body growths, such as Azone (marketed by Nelson Research) and Transcutol (marketed by Gattefossé). These solutions are intended for rendering the skin antiseptic prior to puncturing, for preparation of the operative field, for use by the nursing staff to render their hands antiseptic, and for the treatment of closed infected dermatosis, folliculitis, perionychia or acne.

The products according to the invention can be applied in the form of creams which contain some of the compounds mentioned for the preparation of solutions, together with the fatty substances normally used in the preparation of creams or emulsions. These creams can be used especially for preventing the superinfection of gluteal erythema, eczema, mycosis or acne. The products according to the invention can also be used in shampoos as an antidandruff agent.

The products according to the invention can also be used for the treatment or prevention of sexually transmitted diseases, in the form of pessaries, gynecological tablets or gynecological sponges or as a complement for contraceptives. The pessaries can contain from 0 to 99% of triglycerides, polyethylene glycols of different molecular weights, Tweens, natural or synthetic polymers, polyols and soaps. The gynecological tablets can contain diluents such as lactose or cellulose, lubricants such as magnesium stearate, flow enhancers such as silica, and disintegrating agents such as carboxymethyl starch or cellulose.

The products according to the invention can be administered in the form of sprays with nasal and buccal nozzles for the treatment of infectious syndromes of the respiratory tract (rhinitis, sinusitis, sore throat, tonsillitis, pharyngitis) or in the form of gels or mouthwashes for the treatment of gingivitis and pyorrhea or for the prevention of dental plaque, in which case it is also possible to use toothpastes containing the product according to the invention. The forms for buccal or nasal administration can contain the same excipients as the solutions, to which there may be added flavorings in the case of buccal administration or the constituents necessary for isotonicity in the case of nasal sprays; the toothpastes also contain pyrogenic or non-pyrogenic colloidal silicas, calcium carbonate, sweeteners and fluorine salts.

The products according to the invention can be used in eye lotions, eye solutions or ophthalmic ointments for the treatment of eye infections (for example blepharitis or conjunctivitis) or in contact lens rinsing solutions. These forms for application to the eyes can be prepared using the same constituents as those used for the solutions, care being taken to ensure that the mixture is isotonic.

Furthermore, the products according to the invention can be administered to humans by a general route, for example orally in the form of gelatin capsules or ordinary tablets or in the form of enteric tablets as intestinal antiseptics.

The products according to the invention can also be administered to animals for indications such as the prevention or treatment of infected lesions or lesions capable of becoming superinfected. Here the pharmaceutical compositions are similar to those used in humans, in particular creams, sprays or solutions.

Furthermore, the rapid lethal action of the products according to the invention on germs enables them to be used as surface disinfectants at concentrations which can vary from 0.1 to 4%. In such cases the products are used in preparations such as aqueous or non-aqueous detergent foaming solutions, nebulized sprays or other sprays. Such preparations are particularly useful in the hospital or veterinary sectors and for local authorities or agri-foodstuffs industries. These preparations can contain the same constituents as those used in the antiseptic formulations, although a variety of organic solvents can be added.

Finally, the antimicrobial activity of these products enables them to be used as preservatives in the pharmaceutical, cosmetic and food industries. In such cases the products according to the invention are used as additives for pharmaceutical, cosmetic or food formulations at concentrations which can vary from 0.005 to 0.5%. These compounds can also be used as disinfectant additives in paints.

Different formulations of the products according to the invention can be prepared according to the chosen application. The following Examples illustrate this part of the invention.

EXAMPLE 6

Antiseptic detergent foaming liquid preparation

| | |
|---|---|
| SR 44333 A | 0.5 g |
| Sodium paraffinsulfonate | 15 g |
| Sodium hydroxide or lactic acid qs pH 5.2 | |
| Purified water qs | 100 g |

EXAMPLE 7

Antiseptic alcoholic solution

| | |
|---|---|
| SR 44333 A | 0.5 g |
| Alkyldimethylcarboxy-methylamine (30% solution) | 0.5 g |
| Condensation product of ethylene oxide and propylene glycol L 62 | 1 g |
| Lactic acid or sodium hydroxide qs pH 6.5 | 100 g |
| 70° ethyl alcohol qs | |

EXAMPLE 8

Antiseptic detergent foaming liquid preparation

| | |
|---|---|
| SR 44719 B | 0.1 g |
| Alkyldimethylcarboxy-methylamine (30% solution) | 15 g |
| Disodium tetracemate | 0.1 g |
| Propylene glycol | 20 g |
| Sodium hydroxide qs pH 5.8 | |
| Purified water qs | 100 g |

EXAMPLE 9

Mouthwash

| | |
|---|---|
| SR 44716 A | 0.3 g |
| 95° ethyl alcohol | 14 g |
| Oil of aniseed | 0.00225 ml |
| Eugenol | 0.00075 ml |
| Glycerol | 20 ml |
| Saccharin | 0.03 g |
| Sodium hydroxide solution qs pH 5.5 | |
| Purified water qs | 100 ml |

EXAMPLE 10

Antiseptic pessaries for the treatment of sexually transmitted diseases

| | |
|---|---|
| SR 44719 B | 500 mg |
| Eutectic mixture of fatty acid esters | 2.568 g |

Suppocire A$^R$, marketed by Gattefossé, can be used the eutectic mixture of fatty acid esters.

EXAMPLE 11

Eye lotion

| | |
|---|---|
| SR 44333 A | 0.5 g |
| Sodium chloride | 1.4 g |
| Water for injectable preparations qs | 100 ml |

EXAMPLE 12

Enteric tablets

| | |
|---|---|
| SR 44444 A | 200 mg |
| Hydroxypropylmethyl cellulose 6 cP | 6 mg |
| Lactose | 114 mg |
| Microcrystalline cellulose | 60 mg |
| Sodium carboxymethyl starch | 12 mg |
| Magnesium stearate | 8 mg |
| Weight of finished uncoated tablet | 400 mg |

Coating

| | |
|---|---|
| Eudragit L 100 ® | 0.9 mg |
| Dibutyl phthalate | 0.9 mg |
| Acetone | 14.1 mg |
| Isopropyl alcohol | 14.1 mg |
| Weight of finished coated tablet | 430 mg |

EXAMPLE 13

Spray

| | |
|---|---|
| SR 44719 A | 2 g |
| 95° ethanol | 20 g |
| Propylene glycol | 5 g |
| Na hydroxide qs pH 5.5 | |
| Water qs | 100 g |
| Propellant qs | |

EXAMPLE 14

Film-forming spray

| | |
|---|---|
| SR 44333 B | 0.5 g |
| Polyvinylpyrrolidone | 2 g |
| Acrylic resin | 2 g |
| 95° ethanol qs | 100 g |
| Propellant qs | |

EXAMPLE 15

Antidandruff shampoo

| | |
|---|---|
| Sodium lauryl-ether-sulfate (30% solution) | 21 g |
| Copra diethanolamide | 2 g |
| Polyglycolic acid esters of fatty alcohols | 8 g |
| Linalyl acetate | 0.2 g |
| Sodium chloride | 0.7 g |
| SR 44719 B | 0.1 g |
| Water qs | 100 g |

EXAMPLE 16

A product according to the invention can be used as a preservative in an emulsion cream.

| | |
|---|---|
| Vaseline oil | 6 g |
| Mixture of cetostearyl alcohol and ethoxylated cetostearyl alcohol | 9 g |
| Anhydrous monosodium phosphate | 0.300 g |
| Disodium tetracemate | 0.010 g |
| Vaseline | 15 g |
| SR 44641 A | 0.100 g |
| Phosphoric acid qs pH 4.5 | |
| Purified water qs | 100 g |

EXAMPLE 17

The product according to the invention can be used as a preservative in a cream for cosmetological use.

| | |
|---|---|
| Collagen | 0.500 g |
| Carboxypolymethylene 934 | 0.400 g |
| Hydrogenated lanolin | 4 g |
| Perhydrosqualene | 20 g |
| Polyethoxylated sorbitol monopalmitate | 2 g |
| SR 44444 A | 0.150 g |
| Lactic acid or sodium hydroxide qs pH 6.5 | |
| Purified water qs | 100 g |

EXAMPLE 18

Preservative in a sun oil

| | |
|---|---|
| Mineral oil 65/75 | 68 g |
| Castor oil | 8 g |
| Sesame oil | 20 g |
| Isopropyl alcohol | 2 g |
| Eusolex ® | 1.5 g |
| Fragrance | 0.4 g |
| SR 44719 B | 0.100 g |

(Eusolex ® is marketed by Merck.)

EXAMPLE 19

A product according to the invention can be used as a preservative in a shampoo

| | |
|---|---|
| Potassium amino acid palmitate | 20 g |
| Sodium alkylsulfates | 2 g |
| Copra diethanolamide | 5 g |
| Linalyl acetate | 0.200 g |
| SR 44641 A | 0.05 g |
| Sodium hydroxide qs pH 7 | |
| Purified water qs | 100 g |

EXAMPLE 20

Preservative for fruit juice or jam

| | |
|---|---|
| Micronized SR 44719 A | 0.02% |

EXAMPLE 21

Disinfectant for inert surfaces

| | |
|---|---|
| SR 44333 B | 2 g |
| Dodecyldimethylcarboxy-dimethylamine | 20 g |
| Disodium tetracemate | 2 g |
| Lactic acid qs pH 3.5 | |
| Purified water qs | 100 g |

What is claimed is:

1. A compound of the formula:

$$\text{Ar}-\text{X}-\text{CH}_2-\underset{\underset{\text{OH}}{|}}{\text{CH}}-\text{CH}_2-\text{N}\underset{}{\overset{2\quad 3}{\diagup}}\underset{4}{\diagdown}\text{CH}_2-\underset{}{\bigcirc}-R_1 \quad (I)$$

in which:
- Ar represents a phenyl group substituted by $R_2$, $R_3$ and $R_4$, or a naphth-1-yl or naphth-2-yl group, the said naphthyl groups being unsubstituted or substituted by 1 or 2 halogen atoms;
- X represents an oxygen atom or a sulfur atom;
- $R_1$ represents a hydrogen atom or a halogen atom;
- $R_2$ represents a halogen atom, a trifluoromethyl group, a phenyl group which is unsubstituted or substituted by 1 to 3 halogen atoms, a benzyl group which is unsubstituted or substituted by 1 to 3 halogen atoms, a phenoxy group which is unsubstituted or substituted by 1 to 3 halogen atoms, or an alkyl group containing from 1 to 4 carbon atoms;
- $R_3$ and $R_4$ represent hydrogen, a halogen atom or an alkyl group containing from 1 to 4 carbon atoms; and
- the benzyl group substitutes the piperidino radical in the 2-, 3- or 4-position, or a salt thereof with a mineral or organic acid.

2. A compounds according to claim 1 of formula (I) in which the group Ar is 2,4-dichlorophenyl.

3. 1-(4-Benzylpiperidino)-3-(2,4-dichlorophenoxy)-propan-2-ol or a salt thereof with a mineral or organic acid.

4. 1-(4-Benzylpiperidino)-3-(2,4-dichlorophenoxy)-propan-2-ol methanesulfonate.

5. In a pharmaceutical, disinfectant, cosmetic or veterinary composition which contains an effective antimicrobial, antiseptic or disinfectant amount of an antimicrobial compound as a minor, active ingredient, the improvement wherein said antimicrobial compound is the compound having formula I as claimed in claim 1.

6. The composition of claim 5, which is a pharmaceutical composition having antimicrobial and disinfectant activity, and wherein said effective amount of said antimicrobial compound having formula I is from 0.01 to 5%, and wherein said antimicrobial compound is present in combination with a pharmaceutically acceptable excipient.

7. The composition of claim 5, which is a disinfectant composition for inert surfaces, and wherein said effective disinfectant amount of said antimicrobial compound having formula I is from 0.1 to 4%, and wherein said disinfectant composition further comprises a vehicle.

8. In a pharmaceutical, cosmetic or food composition which contains an effective preservative amount of an antimicrobial compound as a minor, active ingredient, the improvement wherein said antimicrobial compound is the compound having formula I as claimed in claim 1.

9. The composition of claim 8, which is a pharmaceutical composition, and wherein said effective preservative amount of said antimicrobial compound is from 0.005 to 0.5%.

10. The composition of claim 8, which is a cosmetic product amount of said antimicrobial compound is from 0.005 to 0.5%.

11. The composition of claim 8, which is a food product amount of said antimicrobial compound is from 0.005 to 0.5%.

* * * * *